United States Patent [19]
Zeitlin et al.

[11] Patent Number: 5,733,756
[45] Date of Patent: Mar. 31, 1998

[54] LACTAMS AND PROCESSES FOR STEREOSELECTIVE ENRICHMENT OF LACTAMS, AMIDES, AND ESTERS

[75] Inventors: Andrew L. Zeitlin, Millington; David I. Stirling, Branchburg, both of N.J.

[73] Assignee: Celgene Corporation, Warren, N.J.

[21] Appl. No.: 583,317

[22] Filed: Jan. 5, 1996

[51] Int. Cl.$^6$ ............ C12P 17/12; C07D 211/26
[52] U.S. Cl. .............. 435/122; 546/229; 546/230; 546/237; 546/238
[58] Field of Search ................. 546/229, 230, 546/237, 238; 435/122

[56] References Cited

U.S. PATENT DOCUMENTS

| | | | |
|---|---|---|---|
| 2,507,631 | 5/1950 | Hartmann et al. | 260/294 |
| 2,957,880 | 10/1960 | Rometsch | 546/233 |
| 4,992,445 | 2/1991 | Lawter et al. | 514/279 |
| 5,104,899 | 4/1992 | Young et al. | 514/646 |
| 5,114,946 | 5/1992 | Lawter et al. | 514/279 |
| 5,217,718 | 6/1993 | Colley et al. | 424/449 |
| 5,283,193 | 2/1994 | Yamamoto et al. | 435/280 |
| 5,284,769 | 2/1994 | Evans et al. | 435/280 |
| 5,331,000 | 7/1994 | Young et al. | 514/570 |
| 5,362,755 | 11/1994 | Barberich et al. | 514/649 |
| 5,375,693 | 12/1994 | Woosley et al. | 514/317 |
| 5,449,743 | 9/1995 | Kobayashi et al. | 528/355 |

FOREIGN PATENT DOCUMENTS

| | | |
|---|---|---|
| WO 97/03671 | 2/1997 | WIPO. |
| WO 97/03672 | 2/1997 | WIPO. |
| WO 97/03673 | 2/1997 | WIPO. |

OTHER PUBLICATIONS

Bowden, K., Bromley, K., "Reactions of Carbonyl Compounds in Basic Solutions, Part 15. The Alkaline Hydrolysis of N–Methyl, N–Phenyl, and Bicyclo Lactams, Penicillins, and N–Alkyl–N–methylacetamides" J. Chem. Soc. Perkin Trans. 2, 12, pp. 2111–2116, 199, 1990.

Ding, L.K., Irwin, W.J. "cis– and trans–Azetidin–2–ones from Nitrones and Copper Acetylide" J. Chem. Soc. Perkin I, 22, pp. 2382–2386, 1976.

Brown, C. "Chirality in Drug Design and Synthesis", Academic Press Inc., pp. 4–7, 1990.

Klibanov, A.M. "Asymmetric Transformations Catalyzed by Enzymes in Organic Solvents", Acc. Chem. Res., 23, pp. 114–120, 1990.

Hou, J.P., et al. "beta–Lactam Antibiotics: Their Physicochemical Properties and Biological Activities in Relation to Structure" J. Pharm. Sci., vol. 60 (4), pp. 503–532, Apr. 1971.

Angrist et al. Journal of Clinical Phsychopharmacology, 1992 12:268–272.
Barkley et al. Pediatrics 1990 86:184–192.
Barkley et al. Pediatrics 1991 87:519–531.
Golinko Prog. Neuro–Psychopharmacol. & Biol Phsychiat 1984 8:1–8.
Greenhill Pediatric Psychopharmacology 1992 15:1–27.
Scott Drug Safety 1993 8:149–159.
White et al. J. Clin. Phsychiatry 1992 53:153–156.
Biosis Abstract No.: 87129969 Holmes et al. Psychostimulant Response in Aids–Related Complex Patients J. Clin. Psychiatry 50(1):5–8, 1987.
Biosis Abstract No.: 95066168 Srinivas et al. Enantioselective Pharmacoinetics and Pharmacoldynamics of Racemic Threo–Methylphenidate in Children with Attention Deficit Hyperactivity Disorder Clin. Pharmacol. Ther 52(2):561–568, 1995.
Earle et al. J. Chem. Soc. 1969:2093.
Srinivas et al. Enantiomeric Gas Chromatography Assay with Electron Capture Detection for d–Ritalinic Acid in Plasma. J. Chromatagraph 1990 530:327–336.
Srinivas et al. Sterioselective Disposition of Methylphenidate in Children with Attention Deficit Disorder J. Pharmacol. Exp. Ther. 1987 241:300–306.
Corey et al. J. Amer. Chem. Soc 1965 87:2518.
Moll F, Naturforsch Teil B. 1966 21:297.
Greenhill, Pediatric Psychopharmacology 1992 15:1–27.
Scott, Drug Safety 1993 8:149–159.
White et al., J. Clin. Psychiatry 1992 53:153–156.
Greenhill L., Attention–Deficit Hyperactivity Disorder Child & Adol. Psych. Clin. N.A., 1995 4:123–165.
Navia et al., Annals of Neurology 1986 19:517–524.
Douzenis et al., Proc 7th Int'l Conf. AIDS 1991 1:2135–2215.
Aoyama et al., Pharmacolinetics and pharmacodynammics of (+)–threo–methylphenidate enantiomer in patients with hypersomnia Clin. Pharmacol. Ther 1994 55:270–276.
Uetrecht et al., Pharmacol Res. 1989 6:265–273.
Staal et al., Lancet 1992 339:909–912.
Rieder et al., Ann. Intern Med. 1989 110:286–289.
Patrick et al., J. Pharmacol. & Exp. Terhap. 1987 241:152–158.
Srinivas et al., Pharmacol Res. 1993 10:14–21.
Brown G., Int'l J. Psychiatry Med. 1995 25:21–37.

Primary Examiner—C. Warren Ivy
Assistant Examiner—Lyman H. Smith
Attorney, Agent, or Firm—Woodcock Washburn Kurtz Mackiewicz & Norris LLP

[57] ABSTRACT

Novel lactams and processes for the preparation of chiral compounds having utility as intermediates in the synthesis of compounds with Central Nervous System stimulant activity.

20 Claims, No Drawings

LACTAMS AND PROCESSES FOR STEREOSELECTIVE ENRICHMENT OF LACTAMS, AMIDES, AND ESTERS

This invention relates to novel lactams and processes for the preparation of chiral compounds having utility as intermediates in the synthesis of Central Nervous System stimulants.

BACKGROUND OF THE INVENTION

The biological activity of chemical products such as pharmaceuticals and agricultural products which possess a center of chirality often is found to reside principally in one of the possible forms. Since most chemical syntheses are not inherently stereoselective, this poses a serious chemical processing problem. Enrichment in favor of one chiral form thus will be required at some stage, either the final chiral compounds or chemical precursors which possess the same center of chirality.

The acetic acids of the present invention are useful intermediates in the production of (d)-threo-methylphenidate, the (d)-threo-2-(piperid-2-yl)-2-phenyl acetic acid methyl ester of the formula:

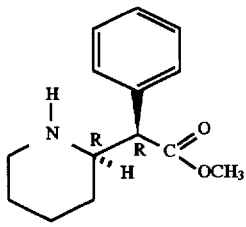

which is a Central Nervous System stimulant useful in the treatment of both Attention Deficit Disorder, cognitive decline in AIDS/AIDS-Related Complex patients, and hypersomnia.

U.S. Pat. No. 2,507,631, to Hartmann et al. describes certain α-aryl-α-piperidyl-(2)-acetic acids and processes for making the same through treatment of monoaryl- and monophenyl-aceto nitriles with nuclear halogenated pyridines or piperidines in the presence of a hydrogen halide eliminating agent.

U.S. Pat. No. 2,957,880, to Rometsch et al. describes the conversion of certain α-aryl-α-piperidyl-(2)-acetic acids and derivatives thereof (including methylphenidate) into their respective racemates.

U.S. Pat. No. 5,283,193 to Yamamoto et al. describes processes for the production of optically active organic acids of the profen class to high enantiomeric excess using certain amidases or nitrile hydratases of microbial origin.

U.S. Pat. No. 5,284,769 to Evans et al. describes the use of an aminoacylase to enrich a racemic mixture of a 5-membered lactam to high enantiomeric excess. Methods for the preparation of chirally pure fused ring beta-lactams are not disclosed.

Bowden et al., *J. Chem. Soc. Perkin. Trans.*, 2:2111–2116 (1990) describe the alkaline hydrolysis of certain N-methyl and N-phenyl lactams and N-alkyl-N-methylacetamides.

Earle et al., *J. Chem. Soc. C.*, 2093 (1969) describes the synthesis and hydrolysis rates of certain β-lactams having fused 1,4 homocyclic rings.

DETAILED DESCRIPTION OF THE INVENTION

The present invention relates to the production of chiral compounds having utility as intermediates in the synthesis of d-threo-methylphenidate by enzymatic and microbial resolution of racemic lactams, amides, esters, and nitriles to yield d-threo-2-(piperid-2-yl)-2-phenyl-acetic acid, commonly known as (d)-ritalinic acid, and their functional optically active acid derivatives such as esters and amides.

More specifically, the present invention relates to the formation of d-threo-2-(piperid-2-yl)-2-phenyl acetic acids through enzymatic conversion of compounds of the formula (I):

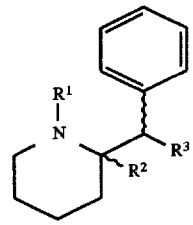

wherein:

{i} $R^1$ and $R^2$ are hydrogen, and $R^3$ is carbamoyl;

{ii} $R^1$ and $R^3$ taken together are carbonyl, and $R^2$ is hydrogen;

{iii} $R^3$ is cyano, and $R^1$ and $R^2$ are hydrogen; or

{iv} $R^1$ and $R^2$ are hydrogen and $R^3$ is carboxy methyl.

In another embodiment the unreacted racemic lactam, amide, or nitrile of formula (I) may be first biocatalytically enriched to high enantiomeric excess and subsequently converted to the optically pure (d)-ritalinic acid.

In either case, the resultant d-threo-2-(piperid-2-yl)-2-phenyl acetic acid intermediate can then be esterified according to known techniques to yield (d)-threo-methylphenidate.

In another embodiment, the dl-threo-2-(piperid-2-yl)-2-phenyl acetic acid methyl ester may be enriched by action of an esterase directly to d-threo-2-(piperid-2-yl)-2-phenyl acetic acid methyl ester (d-threo-methylphenidate) substantially free of the 1-isomer, and recovered.

In a first embodiment, wherein $R^1$ and $R^2$ are hydrogen, and $R^3$ is carbamoyl (i.e., $CONH_2$), the compound is converted to d-threo-2-(piperid-2-yl)-2-phenyl acetic acid substantially free of the 1-isomer by action of an amidase.

In a second embodiment, wherein $R^1$ and $R^3$ taken together are carbonyl, and $R^2$ is hydrogen, the compound is converted to d-threo-2-(piperid-2-yl)-2-phenyl acetic acid substantially free of the 1-isomer by action of an amidase or lactamase.

In a third embodiment, wherein $R^3$ is cyano, and $R^1$ and $R^2$ are hydrogen, the compound is converted to d-threo-2-(piperid-2-yl)-2-phenyl acetic acid substantially free of the 1-isomer by action of a nitrilase.

In a fourth embodiment, wherein $R^3$ is cyano, and $R^1$ and $R^2$ are hydrogen, the compound can be converted to the amide by the action of a nitrile hydratase, which amide is then converted to d-threo-2-(piperid-2-yl)-2-phenyl acetic acid substantially free of the 1-isomer by action of an amidase.

In yet another embodiment, wherein $R^1$ and $R^2$ are hydrogen and $R^3$ is carboxy methyl (i.e., $COOCH_3$), the compound can be enriched directly to d-threo-2-(piperid-2-yl)-2-phenyl acetic acid methyl ester substantially free of the 1-isomer by action of an esterase.

The present invention also relates to novel lactams useful as intermediates in the production of d-threo-2-(piperid-2-yl)-2-phenyl acetic acid and derivatives thereof, and methods for producing the same.

The term "enantiomeric enrichment" as used herein refers to the increase in the amount of one enantiomer as compared to the other. This can involve (i) a decrease in the amount of one chiral form as compared with the other, (ii) an increase in the amount of one chiral form as compared with the other, or (iii) a decrease in the amount of one chiral form and an increase in the amount of the other chiral form.

A "substantial amount" of conversion as used herein is defined as being at least 50% by weight of enantiomeric conversion.

The term, "substantially free of the 1-isomer" means that the composition contains at least 90% by weight of d-threo-2-(piperid-2-yl)-2-phenyl acetic acid, and 10% by weight of 1-threo-2-(piperid-2-yl)-2-phenyl acetic acid or derivative thereof. In the most preferred embodiment, the term "substantially free of the 1-isomer" means that the composition contains at least 99% by weight of d-threo-2-(piperid-2-yl)-2-phenyl acetic acid and 1% or less of 1-threo-2-(piperid-2-yl)-2-phenyl acetic acid or derivative thereof.

The lactamases or cyclicamidases, nitrilases, nitrile hydratases, and esterases described herein can be obtained from microorganisms of the genera Alcaligenes, Pseudomonas, Rhodopseudomonas, Corynebacterium, Escherichia, Arthrobacter, Aspergillus, Acinetobacter, Brevibacterium, Bacillus, Mycobacterium, Rhodococcus, Agrobacterium, Botrytis, Candida, Chaetomium, Chromobacterium, Cladosporium, Enterobacter, Microbacteriumr Mucor, Nocardia, Ophiobolus, Penicillium, Rhizopus, Rhodotorula, Saccharomyces, Staphylococcus, Streptomyces, Torulopsis, and Trichoderma, or preparations thereof.

More preferably, the lactamases or cyclicamidases, nitrilases, nitrile hydratases, and esterases described herein can be obtained from *Pseudomonas cepacia, Acinetobacter baumanni, Pseudomonas putida, Alcaligenes faecalis, Agrobacterium radiobacter, Aspergillus niger, Chromobacterium violaceum, Escherichia coli, Gotrichum candidum, Humicola lanuginosa, Mycobacterium phlei, Nocardia asteroides, Nocardia erythropolis, Penicillium cyclopium, Pseudomonas fluorescens, Pseudomonas ovalis, Pseudomonas putida, Rhizopus niveus, Rhizopus oryzae, Staphylococcus aureus, Streptomyces clavuligerus, Rhodococcus rhodocris* or *Streptomyces griseus*.

The actual enzymatic conversion can be effected by conventional culturing techniques in the presence of the compound of formula (I), with isolated but non-growing cells, or by bringing the compounds into contact with a soluble enzyme preparation. The enzymes described herein can be in free form, either as a cell free extract or a whole cell preparation, or immobilized on a suitable support or matrix such as cross-linked dextran or agarose, silica, polyamide or cellulose. They can also be encapsulated in polyacrylamide, alginates, fibers, or the like. Methods for such immobilization are described in the literature (see, e.g., *Methods of Enzymology*, 44, 1976).

Procedures and materials used herein are described below, followed by typical examples.

PROCEDURES AND MATERIALS

Standard Salt Medium (hereinafter, "Media A")

A suitable salt medium for the microbiological transformations described in the following examples has the following composition:

| Media A: | |
|---|---|
| $MgSO_4$ | 1.00 g/L |
| $CaCl_2$ | 0.021 g/L |

—continued

| Media A: | |
|---|---|
| $ZnSO_4 \cdot 7H_2O$ | 0.20 mg/L |
| $MnSO_4 \cdot 4H_2O$ | 0.10 mg/L |
| $H_3BO_3$ | 0.02 mg/L |
| $CuSO_4 \cdot 5H_2O$ | 0.10 mg/L |
| $CoCL_2 \cdot 6H_2O$ | 0.05 mg/L |
| $NiCl_2 \cdot 6H_2O$ | 0.01 mg/L |
| $FeSO_4$ | 1.50 mg/L |
| $NaMoO_4$ | 2.00 mg/L |
| Fe EDTA | 5.00 mg/L |
| $KH_2PO_4$ | 20.00 mg/L |
| NaOH | to pH 7 |

The composition is not critical but is standardized for all procedures to eliminate it as a variable.

Enrichment and isolation of Sources for Nitrilase, Amidase, and Lactamase biocatalysts.

A chemostat is maintained with 0.5% (w/v) of 2-phenylacetonitrile and 10 mM sodium pyruvate at a dilution rate of 0.3/hr in Media A. The chemostat is inoculated and run for approximately one month at 37° C. and pH 6.8–7.0. Strains which develop are isolated and grown on minimal media agar containing the standard salt medium (Media A) supplemented with 10 mM of pyruvate and 5 mM ∝-aryl-∝-piperidyl-acetonitrile.

Microbial sources for an amidase or nitrile/amidase may also be enriched and isolated by use of shaker flasks maintained on Media A, at pH 6.8–7.0 at 37° C. on an environmental shaker. The isolation technique is performed as above.

Lactamase is enriched and isolated as above using (±) trans-7-phenyl-1-azabicyclo(4,2,0)octan-8-one as the sole nitrogen source instead of 2-phenylacetonitrile or ∝-aryl-∝-piperidyl-acetonitrile.

Enzyme Recovery

Unless otherwise indicated, cells from culture are centrifuged for 10 minutes at 10,000 G, resuspended in 10 mM of phosphate buffer at pH 7 and 0.5 mM of pyridoxal phosphate, and ruptured by two passes through a chilled French press operating at 15,000 psi. Cell debris is removed by centrifugation for one hour at 10,000 G and the enzyme-containing supernatant collected.

Quantitative Analysis

Quantitative analysis of dl-threo-ritalinic acid in biological liquids is performed according to the method of Srinivas et al., Enantiomeric Gas Chromatography Assay with Electron Capture Detection for dl-Ritalinic Acid in Plasma, *J. Chromatagraph.* 530:327–336 (1990). Quantitative analysis of dl-threo-methylphenidate in biological liquids is performed according to the method of Srinivas et al., Stereoselective Disposition of Methylphenidate in Children with Attention Deficit Disorder, *J. Pharmacol. Exp. Ther.*, 241:300–306 (1987).

The following examples will serve to further typify the nature of the invention, but should not be construed as a limitation on the scope thereof, which is defined solely by the appended claims.

EXAMPLE 1

Preparation of (d)-threo-2-(piperid-2-yl)-2-phenyl-acetic acid from trans-7-phenyl-1-azabicyclo (4,2,0)-octan-8-one Preparation of Biocatalyst Lactamase is obtained from *Pseudomonas cepacia* grown on 1–2% penicillin as the sole carbon and nitrogen source in a minimal media. Fifty milliliters of Media A containing 2 g/l of penicillin and is inoculated with *Pseudomonas cepacia*. After the mixture is incubated at 30° C. for 48 hours, 10 mL of the mixture are subcultured into 250 mL of Media A with 2 g/l penicillin. After 40 hours of incubation at 30° C., the cells are concentrated to a paste by centrifugation at 10,000 G and washed with 50 mL phosphate buffer pH 7 and again concentrated to a paste by centrifugation at 10,000 G. The washed paste then is passed through a French Press at 17,000 psi to rupture the cells and produce cell extract. Cell debris is removed by centrifugation for one half hour at 100,000 G and the enzyme-containing supernatant collected.

Racemic (±)trans-7-phenyl-1-azabicyclo(4.2.0)octan-8-one (0.5 g) is added to a mixture of 20 mL of 50 mM potassium phosphate buffer pH 7 and 1 mL cell extract of lactamase. The reaction is maintained at 30° C. until the enantiomer excess as determined by chiral gas chromatography is no less than 98% of d-ritalinic acid obtained, generally about 3 hours under these conditions. A lactamase with opposite stereoselectivity obtained from a microorganism such as *Rhodococcus rhodochrous* can be used to resolve (±)trans-7-phenyl-1-azabicyclo(4,2,0)-octan-8-one to 1-ritalinic acid and the d-trans-7-phenyl-1-azabicyclo(4, 2,0)-octan-8-one. This lactam is then hydrolyzed to the d-ritalinic acid by conventional means.

Trans-7-phenyl-1-azabicyclo (4,2,0) -octan-8-one may be prepared by the method of Corey, Mol, or Earle (Corey et al., *J. Amer. Chem. Soc.*, 87:2518 (1965); Earle et al., *J. Chem. Soc. C.* 2093 (1969); Moll F. Naturforsch., Teil B, 21:297 (1966).

Isolation of (d)-lactam

The reaction mixture prepared above is extracted with methylene chloride and the organic layer is dried with MgSO$_4$. The organic layer is then filtered and concentrated by rotary evaporation at 30° with reduced pressure, to yield an oil product. The oil product may be further purified by column chromatography.

EXAMPLE 2

Preparation of d-threo-2-(piperid-2-yl)-2-phenyl acetic acid from threo-2-(piperid-2-yl)-2-phenyl-2-acetamide Preparation of Amidase Amidase is obtained from *Acinetobacter baumanni* grown on 30 mM 2-cyanobutane as the sole carbon and nitrogen source in a minimal media. Fifty milliliters of Media A containing 30 mM 2-cyanobutane is inoculated with *Acinetobacter baumanni*. After the mixture in incubated at 30° C. for 48 hours, 10 mL of the mixture are subcultured into 250 mL of Media A with 30 mM 2-cyanobutane. After 40 hours of incubation at 30° C., the cells are concentrated to a paste by centrifugation at 10,000 G and washed with 50 mL phosphate buffer pH 7.5 and again concentrated to a paste by centrifugation at 10,000 G. The washed paste then is passed through a French Press at 17,000 psi to rupture the cells and produce cell extract. Cell debris is removed by centrifugation for one half hour at 100,000 G and the enzyme-containing supernatant collected.

Racemic threo-2-(piperid-2-yl)-2-phenyl-2-acetamide (0.5 g) prepared by, e.g., the method of Hartmann (U.S. Pat. No. 2,507,631) is added to a mixture of 20 mL of 50 mM potassium phosphate buffer pH 8 and 1 mL cell extract of amidase. The reaction is maintained at 30° C. until the enantiomer excess as determined by chiral gas chromatography is no less than 98% of d-ritalinic acid is obtained, generally about 5 hours under these conditions. An amidase with opposite stereoselectivity obtained from a microorganism such as *Rhodococcus rhodochrous* can be used to resolve dl-threo-2-(piperid-2-yl)-2-phenyl-acetamide to 1-ritalinic acid and the d-threo-2-(piperid-2-yl)-2-phenyl-acetamide. This amide is then hydrolyzed to the d-ritalinic acid by conventional means.

EXAMPLE 3

Preparation of (d)-threo-2-(piperid-2-yl)-2-phenyl acetic acid from trans-7-phenyl-1-azabicyclo(4,2,0)-octan-8-one Racemic trans-7-phenyl-1-azabicyclo(4,2,0)-octan-8-one (0.5 g) is added to a mixture of 20 mL 50 mM phosphate buffer pH 7.5 and 1 mL of *Pseudomonas putida* cell extract. The reaction is maintained at 30° C. until the enantiomeric excess as determined by gas chromatography is not less than 98% ritalinic acid is obtained, generally about 24 hours under these conditions. Alternatively, a cell extract containing an amidase of opposite stereoselectivity may be used to effect a resolution of racemic trans-7-phenyl-1-aza-bicyclo (4,2,0)-octan-8-one where 1-ritalinic acid is produced and the d-lactam is isolated as the product.

Isolation of (d)-lactam

The reaction mixture prepared above is extracted with methylene chloride and the organic layer dried with MgSO$_4$. The organic layer is then filtered and concentration by rotary evaporation at 30° with reduced pressure, to yield an oil. The oil product may be further purified by column chromatography.

EXAMPLE 4

Preparation of (d)-threo-2-(piperid-2-yl)-2-phenyl-acetic acid from trans-2-(piperid-2-yl)-2-phenyl-acetonitrile Nitrile hydratase and amidase are obtained from *Alcaligenes faecalis* grown on 30 mM 2-cyanobutane or 2-phenylacetonitrile as the sole carbon and nitrogen source in a minimal media. Fifty milliliters of Media A containing 30 mM 2-cyanobutane is inoculated with *Alcaligenes faecalis*. After the mixture is incubated at 30° C. for 48 hours, 10 mL of the mixture are subcultured into 250 mL of Media A with 30 mM 2-cyanobutane or 2-phenylacetonitrile. After 40 hours of incubation at 30° C., the cells are concentrated to a paste by centrifugation at 10,000 G and washed with 50 mL phosphate buffer pH 7.5 and again concentrated to a paste by centrifugation at 10,000 G. The washed paste then is passed through a French Press at 17,000 psi to rupture the cells and produce cell extract. Cell debris is removed by centrifugation for one half hour at 100,000 G and the enzyme-containing supernatant collected.

Use of nitrile hydratase and amidase pathway to produce d-threo-2-(piperid-2-yl)-2-phenyl-acetic acid and 1-threo-2-(piperid-2-yl)-2-phenyl-2-acetamide from d,1-threo-2-(piperid-2-yl)-2-phenyl-acetonitrile.

Racemic threo-2-(piperid-2-yl)-2-phenyl-2-acetonitrile (0.5 g) is added to a mixture of 20 mL of 50 mM potassium phosphate buffer pH 8 and 1 mL cell extract of *Alcaligenes faecalis* with nitrile hydratase and amidase activity. The reaction is maintained at 30° C. until the enantiomer excess as determined by chiral gas chromatography is no less than 98% of d-ritalinic acid is obtained, generally about 5 hours under these conditions.

EXAMPLE 5

The use of an esterase/lipase for the stereoselective enrichment of d1-threo-α-phenyl-α-piperidyl-acetic acid methyl ester A microbial source of a stereoselective esterase or lipase may be obtained from commercial sources such as Novo Nordisk's "Humicola lipolase" or an ATCC Pseudomonas strain 31809 or 31808.

Esterase/lipase is obtained from Pseudomonas sp. ATCC strain 31809 grown on 1% olive oil in media A supplemented with 8 g/L nutrient broth. Fifty milliliters of media A containing the 1% olive oil and 8 g/L nutrient broth is inoculated with Pseudomonas sp. ATCC strain 31809. After the mixture is incubated at 30° C. for 48 hours, 10 mL of the mixture are subcultured into 250 mL of media with 1% olive oil supplemented with 8 g/L nutrient broth. After 24 hours of incubation at 30° C., the cells are concentrated to a paste by centrifugation at 10,000 G and washed with 50 mL phosphate buffer pH 7.5 and again concentrated to a paste. Cells are ruptured as above.

dl-threo-α-phenyl-α-piperidyl-acetic acid methyl ester (0.5 g) prepared by the method of Hartmann is added to a mixture of 20 mL of 50 mM potassium phosphate buffer pH 7 and 1 mL cell extract. The reaction is maintained at 30° C. until an enantiomeric excess as determined by chiral GC of no less than 98% d-threo-methylphenidate is obtained, generally about 25 hours under these conditions.

What is claimed is:

1. A process for producing d-threo-2-(piperid-2-yl)-2-phenyl acetic acid comprising bringing a compound of the formula (I):

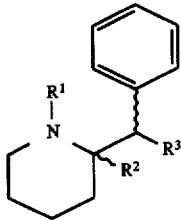

wherein $R^1$ and $R^2$ are hydrogen, and $R^3$ is carbamoyl into contact with an amidase at least until a substantial amount of said compound is converted to d-threo-2-(piperid-2-yl)-2-phenyl acetic acid substantially free of the 1-isomer, and recovering said d-threo-2-(piperid-2-yl)-2-phenyl acetic acid or a derivative thereof.

2. The process according to claim 1 wherein the amidase is of microbial origin.

3. The process according to claim 2 wherein the amidase is obtained from a microorganism selected from the group consisting of Alcaligenes, Pseudomonas, Rhodopseudomonas, Corynebacterium, Escherichia, Arthrobacter, Aspergillus, Acinetobacter, Brevibacterium, Bacillus, Mycobacterium, Rhodococcus, Agrobacterium, Botrytis, Candida, Chaetomium, Chromobacterium, Cladosporium, Enterobacter, Microbacterium, Mucor, Nocardia, Ophiobolus, Penicillium, Rhizopus, Rhodotorula, Saccharomyces, Staphylococcus, Streptomyces, Torulopsis, and Trichoderma.

4. The process according to claim 1 wherein the unreacted amide is recovered.

5. A process for producing d-threo-2- (piperid-2-yl)-2-phenyl acetic acid comprising bringing a compound of the formula (I):

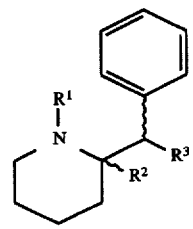

wherein $R^1$ and $R^3$ taken together are carbonyl, and $R^2$ is hydrogen into contact with at least one of an amidase or lactamase at least until a substantial amount of said compound is converted to d-threo-2-(piperid-2-yl)-2-phenyl acetic acid substantially free of the 1-isomer, and recovering said d-threo-2-(piperid-2-yl)-2-phenyl acetic acid or a derivative thereof.

6. The process according to claim 5 wherein the amidase or lactamase is of microbial origin.

7. The process according to claim 6 wherein the amidase or lactamase is obtained from a microorganism selected from the group consisting of Alcaligenes, Pseudomonas, Rhodopseudomonas, Corynebacterium, Escherichia, Arthrobacter, Aspergillus, Acinetobacter, Brevibacterium, Bacillus, Mycobacterium, Rhodococcus, Agrobacterium, Botrytis, Candida, Chaetomium, Chromobacterium, Cladosporium, Enterobacter, Microbacterium, Mucor, Nocardia, Ophiobolus, Penicillium, Rhizopus, Rhodotorula, Saccharomyces, Staphylococcus, Streptomyces, Torulopsis, and Trichoderma, or preparations thereof.

8. The process according to claim 5 wherein the unreacted (d)-trans-7-phenyl-1-azabicyclo(4,2,0)-octan-8-one is recovered.

9. A process for producing d-threo-2-(piperid-2-yl)-2-phenyl acetic acid comprising bringing a compound of the formula (I):

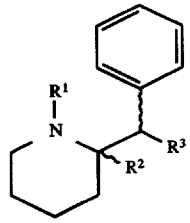

wherein $R^3$ is cyano, $R^1$ and $R^2$ are hydrogen, into contact with a nitrilase at least until a substantial amount of said compound is converted to d-threo-2-(piperid-2-yl)-2-phenyl acetic acid substantially free of the 1-isomer, and recovering said d-threo-2-(piperid-2-yl)-2-phenyl acetic acid or a derivative thereof.

10. The process according to claim 9 wherein the nitrilase is of microbial origin.

11. The process according to claim 10 wherein the nitrilase is obtained from a microorganism selected from the group consisting of Alcaligenes, Pseudomonas, Rhodopseudomonas, Corynebacterium, Escherichia, Arthrobacter, Aspergillus, Acinetobacter, Brevibacterium, Bacillus, Mycobacterium, Rhodococcus , Agrobacterium, Botrytis , Candida, Chaetomium, Chromobacterium, Cladosporium, Enterobacter, Microbacterium, Mucor, Nocardia, Ophiobolus, Penicillium, Rhizopus, Rhodotorula, Saccharomyces, Staphylococcus, Streptomyces, Torulopsis, and Trichoderma or preparations thereof.

12. A process for producing d-threo-2-(piperid-2-yl)-2-phenyl acetic acid comprising bringing a compound of the formula (I):

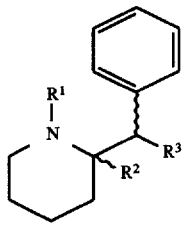

wherein $R^3$ is cyano, and $R^1$ and $R^2$ are hydrogen, into contact with a nitrile hydratase and amidase at least until a substantial amount of said compound is converted to d-threo-2-(piperid-2-yl)-2-phenyl-acetic acid substantially free of the l-isomer, and recovering said d-threo-2-(piperid-2-yl)-2-phenyl acetic acid or a derivative thereof.

13. The process according to claim 12 wherein the nitrile hydratase is of microbial origin.

14. The process according to claim 13 wherein the nitrile hydratase and amidase are obtained from at least one microorganism selected from the group consisting of Alcaligenes, Pseudomonas, Rhodopseudomonas, Corynebacterium, Escherichia, Arthrobacter, Aspergillus, Acinetobacter, Brevibacterium, Bacillus, Mycobacterium, Rhodococcus, Agrobacterium, Botrytis, Candida, Chaetomium, Chromobacterium, Cladosporium, Enterobacter, Microbacterium, Mucor, Nocardia, Ophiobolus, Penicillium, Rhizopus, Rhodotorula, Saccharomyces, Staphylococcus, Streptomyces, Torulopsis, and Trichoderma or preparations thereof.

15. A process according to claim 12 wherein the unreacted d-threo-2-(piperid-2-yl)-2-phenyl acetamide is recovered.

16. A process for producing d-threo-2-piperid-2-yl)-2-phenyl acetic acid methyl ester comprising bringing a compound of the formula (I):

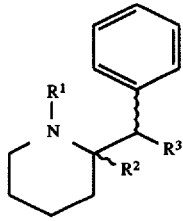

wherein $R^1$ and $R^2$ are hydrogen, and $R^3$ is carboxy methyl, into contact with an esterase at least until a substantial amount of said compound is enriched to d-threo-2-piperid-2-yl)-2-phenyl acetic acid methyl ester substantially free of the l-isomer, and recovering said methyl ester.

17. The process according to claim 16 wherein the esterase is of microbial origin.

18. The process according to claim 17 wherein the esterase is obtained from a microorganism selected from the group consisting of Alcaligenes, Pseudomonas, Rhodopseudomonas, Corynebacterium, Escherichia, Arthrobacter, Aspergillus, Acinetobacter, Brevibacterium, Bacillus, Mycobacterium, Rhodococcus, Agrobacterium, Botrytis, Candida, Chaetomium, Chromobacterium, Cladosporium, Enterobacter, Microbacterium, Mucor, Nocardia, Ophiobolus, Penicillium, Rhizopus, Rhodotorula, Saccharomyces, Staphylococcus, Streptomyces, Torulopsis, and Trichoderma or preparations thereof.

19. A process for producing a d-threo amide of the formula

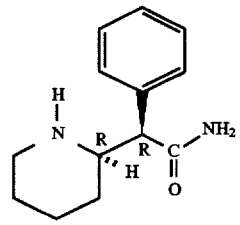

comprising contacting a racemic amide of the formula

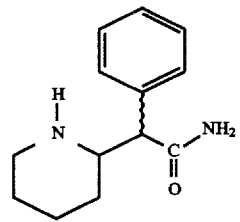

with an amide at least until a substantial amount of said racemic amide is resolved to said d-threo amide.

20. A process for producing a d-threo acid of the formula

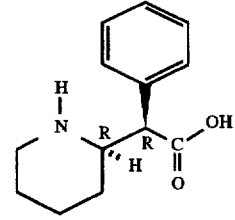

comprising contacting an amide of the formula

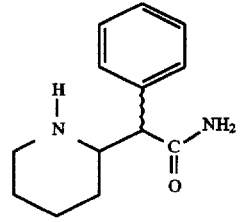

with an amidase at least until a substantial amount of said racemic amide is converted to said d-threo acid.

* * * * *